United States Patent [19]
Carter

[11] Patent Number: 5,477,730
[45] Date of Patent: Dec. 26, 1995

[54] ROLLING ELEMENT BEARING CONDITION TESTING METHOD AND APPARATUS

[76] Inventor: Duncan L. Carter, P.O. Box 3394, Boulder, Colo. 80307

[21] Appl. No.: 118,118

[22] Filed: Sep. 7, 1993

[51] Int. Cl.$^6$ ................................................ G01N 29/04
[52] U.S. Cl. ................................ 73/609; 73/660; 73/593
[58] Field of Search ........................... 73/593, 609, 660; 364/507

[56] References Cited

U.S. PATENT DOCUMENTS

4,419,897  12/1983  Matsuoka ................................. 73/660
4,488,240  12/1984  Kapadia ................................... 73/660

*Primary Examiner*—Hezron E. Williams
*Assistant Examiner*—Christine K. Oda
*Attorney, Agent, or Firm*—John R. Flanagan

[57] ABSTRACT

The rolling element bearing condition testing method uses acceleration signals at frequencies over 1000 Hertz and employs band-pass and digital filtering and envelope detecting techniques. The testing method measures the vibration signals generated by the rolling element bearing in the frequency range containing the majority of the rolling bearing energy, typically from 2,000 Hertz to 15,000 Hertz, next optionally de-modulates those signals, and then uses digital filter techniques to remove the interference, either from the de-modulated acceleration signal or from the raw acceleration signal. The different digital filtering techniques applied by the testing method are as follows: first, separating interfering signals from the rolling element bearing output signals; second, determining the frequencies of the interfering frequencies to be removed; and, third, compensating the amplitude of rolling element bearing output signals for the portions of the rolling element bearing signals removed with the interference.

18 Claims, 14 Drawing Sheets

ROLLING ELEMENT BEARING CONDITION TESTING METHOD AND APPARATUS

BACKGROUND OF THE INVENTION

1. Field of the Invention

The present invention generally relates to techniques for vibration testing of rolling element bearings in rotating machinery and, more particularly, is concerned with an improved method and apparatus for testing rolling element bearing condition.

2. Description of the Prior Art

The condition of rolling element (ball, roller, etc.) bearings used in rotating machinery is commonly assessed by measuring vibration acceleration signals generated by the rolling element bearings during machinery operation. While the signals which rolling element bearings produce contain energy throughout the spectrum, the majority of the energy is found in a band of frequencies typically ranging from a low frequency of 2,000 to 3,000 Hertz up to a high frequency ranging from 10,000 to 15,000 Hertz, using acceleration as a parameter.

Common measurement practice uses information derived from measuring the peak and average levels of signals in the time-domain and average levels derived from the frequency domain data of the same signals. Envelope detection, or de-modulation, of these signals for purposes of analysis is also a common practice.

Spectral analysis of the envelope detected signals is also commonly used as a method for distinguishing signal frequencies, calculable from bearing geometry, produced by rolling element bearing flaws, from interference signals although this method has several disadvantages. Spectral analysis returns only average information about the signals. Flawed rolling element bearings produce modified impulse type signals with high peak to average ratios. Spectrum analysis provides no information about peak signal levels, a good indicator of the potential for new or increased rolling element bearing damage and also for damage to the surrounding machine structures. In addition, dependence on spectral analysis of the raw signal or the envelope-detected signals before flawing occurs provides minimal information about causes of rolling element bearing damage including loss of clearance and inadequate lubrication.

Without interfering signals from other machine sources, analysis of the signals produced by the rolling element bearings is relatively simple. Since most machine interfering signals decrease more rapidly with increased frequency than the rolling element bearing signals, prior art practice typically minimizes, but does not eliminate, interference by measuring the signals at frequencies higher than the low frequency end of spectrum produced by the rolling element bearings. Because the rolling element bearing signals are attenuated rapidly with distance and more rapidly as measurement frequency is increased, reducing or eliminating the lower frequency portion of the spectrum used in the measurements adds significant error and uncertainty to the signal amplitude information.

Consequently, a need still exists for a method of testing rolling element bearing condition which will provide reliable and early detection of rolling element bearing flaws.

SUMMARY OF THE INVENTION

The present invention provides a method and apparatus for testing rolling element bearing condition which satisfies the above-noted needs by using acceleration signals at frequencies over about 1000 Hertz and by employing band-pass and digital filtering and envelope detecting techniques which overcomes the aforementioned disadvantages associated with the prior art practices. The testing method and apparatus eliminates the need to reduce interference by filtering or suppressing the low frequency end of the rolling element bearing signal spectrum and thus improves the accuracy and reliability of the measurement process. Also, the testing method and apparatus may be applied to either demodulated time domain vibration signals or raw vibration signals.

Accordingly the present invention is directed to a rolling element bearing condition testing method and apparatus which measures the time domain vibration signals generated by a rolling element bearing in a frequency range containing the majority of the rolling element bearing energy, typically from about 2,000 to 15,000 Hertz. The testing method and apparatus include the operative steps of: detecting raw vibration signals from a rolling element bearing, optionally, band pass filtering the raw vibration signals to provide output signals in the range of from about 2,000 to 15,000 Hertz, optionally de-modulating (or envelope detecting) the band pass filtered output signals to provide a demodulated (or envelope detected) output signals, and then applying a selected one of a plurality of digital filtering techniques to remove the interference, either from the de-modulated or raw signals, and applying the digitally filtered signal to a display, storage or processor.

The different digital filtering techniques applied by the testing method and apparatus are as follows: first, separating interfering signals from the rolling element bearing output signals; second, determining the frequencies of the interfering frequencies to be removed; and, third, compensating the amplitude of rolling element bearing output signals for the portions of the rolling element bearing signals removed with the interference. The compensating step may be omitted in some cases. In the case of envelope detected signals, as opposed to raw signals, the testing method also includes the step of: fourth, reducing the average value of the rolling element bearing output signal corresponding to the reduction of the average level of the interference.

These and other features and advantages of the present invention will become apparent to those skilled in the art upon a reading of the following detailed description when taken in conjunction with the drawings wherein there is shown and described an illustrative embodiment of the invention.

DETAILED DESCRIPTION OF THE INVENTION

Overall

Figure 1A:
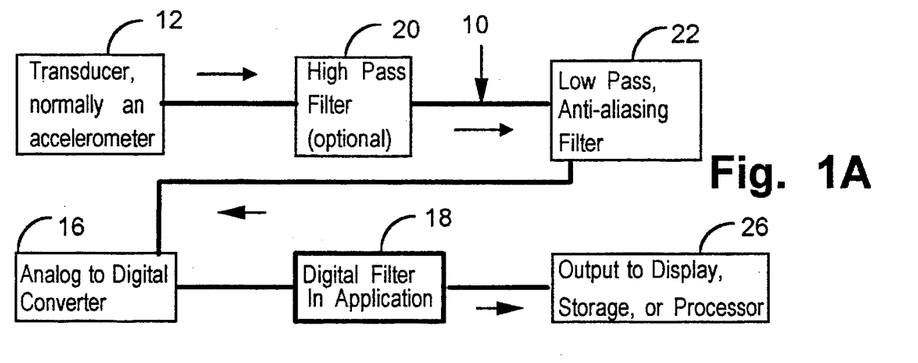
FIG. 1A is a block diagram of a first embodiment of the rolling element bearing condition testing method and apparatus of the present invention.
Figure 1B:
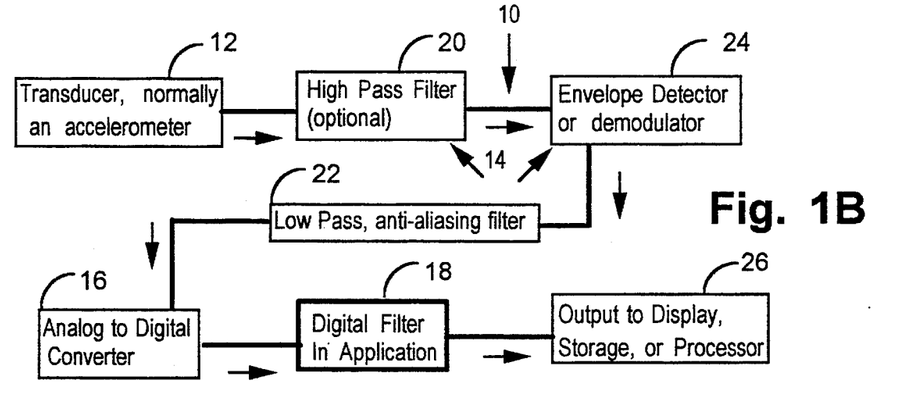
FIG. 1B is a block diagram of a second embodiment of the testing method and apparatus of the present invention.
Figure 1C:
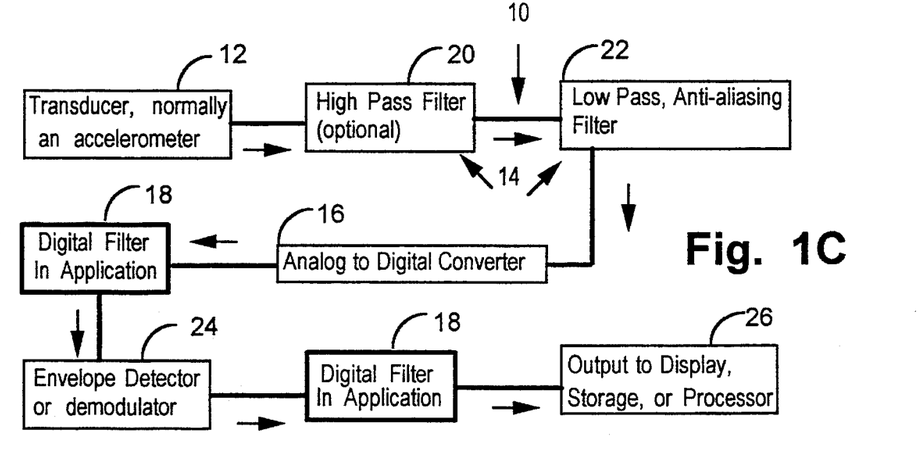
FIG. 1C is a block diagram of a third embodiment of the testing method and apparatus of the present invention.

Referring to the drawings and particularly to FIGS. 1A through 1C, there is illustrated in block diagram form three embodiments of the rolling element bearing condition testing method and apparatus 10 of the present invention for measuring the time domain vibration signals generated by a rolling element bearing in a frequency range containing the majority of the rolling element bearing energy. Basically, each embodiment of the rolling element bearing condition testing apparatus 10 includes means 12, in the form of a transducer and preferably an accelerometer, for detecting acceleration signals emitted from the rolling element bearing at frequencies over 1000 Hertz and first, second and third means 14, 16, 18 arranged in sequence for respectively carrying out the steps of band pass filtering, analog to digital converting, and digital filtering. As shown in FIG. 1A, in the first embodiment of the testing apparatus 10, the first band pass filtering means 14 preferably includes a high pass filter 20 and a low pass, anti-aliasing, filter 22. As shown in FIG. 1B, in the second embodiment of the testing apparatus 10, the band pass filtering means 14 includes the high pass filter 22 and low pass, anti-aliasing, filter 22 and also an envelope detecting or demodulating means 24 interposed between them. As shown in FIG. 1C, the third embodiment of the testing apparatus 10 is a combination of the first and second embodiments thereof. In the basic combination of the present invention, the band pass filtering means 14 can be considered as optional in view that the same filtering can be achieved in the digital filtering means 18.

Figure 3:
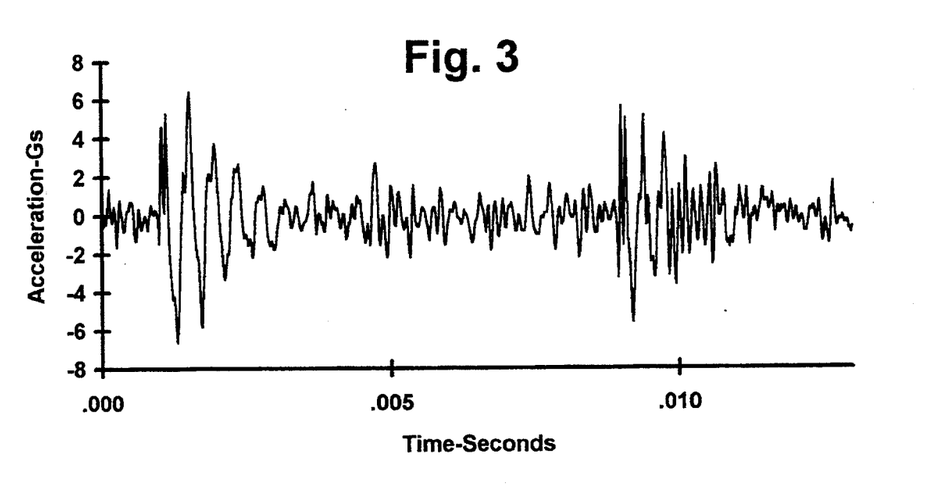
FIG. 3 is a graph depicting the raw acceleration signal generated from a typical flawed rolling element bearing.
Figure 4:
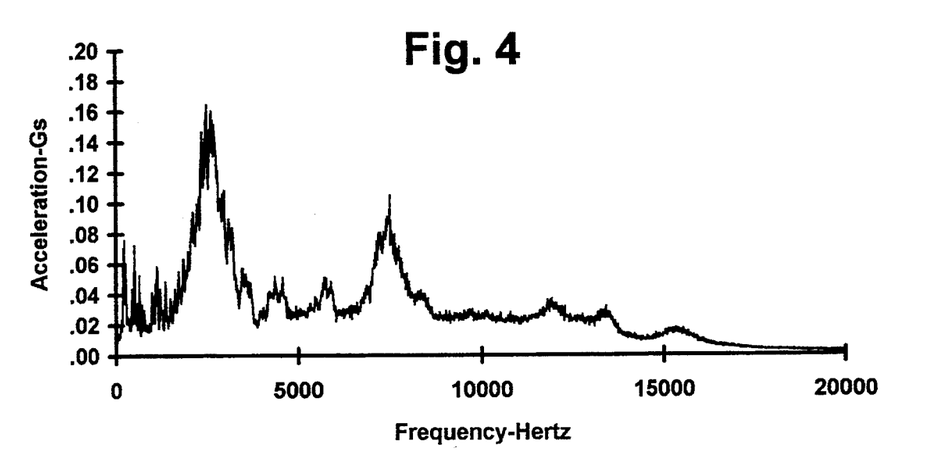
FIG. 4 is a graph depicting the spectrum of the signal of FIG. 3.
Figure 5:
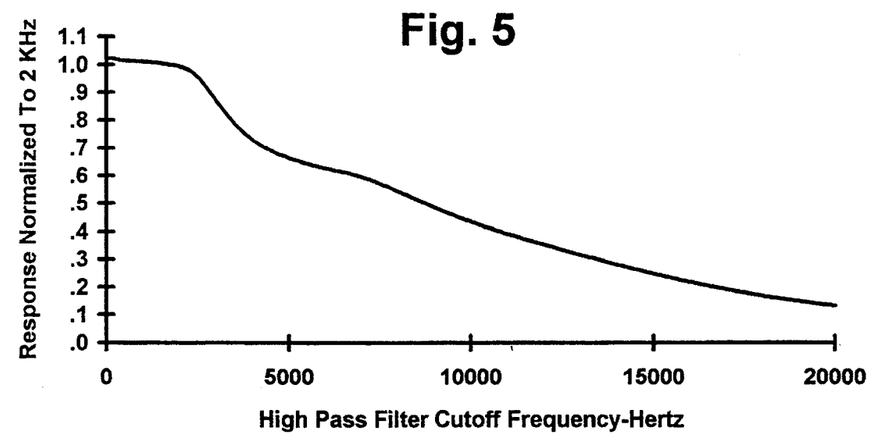
FIG. 5 is a graph depicting the relative response of a typical rolling element bearing high pass filtered signal having a short measurement path between the bearing and the transducer.
Figure 6:
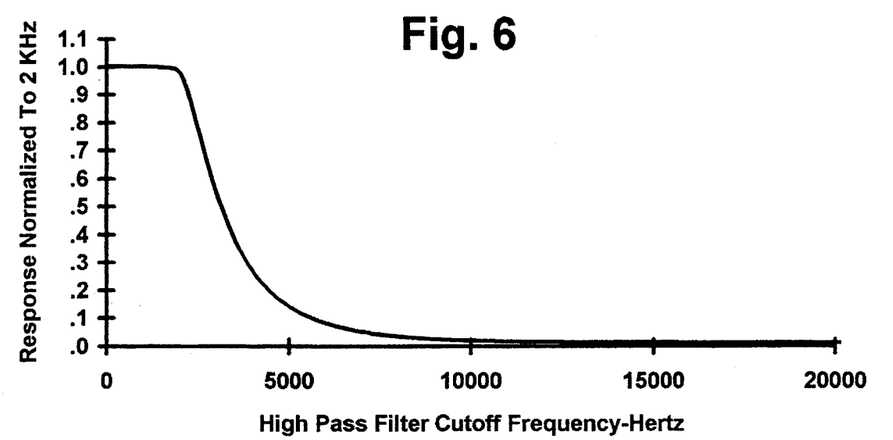
FIG. 6 is a graph similar to FIG. 5 but for a long measurement path.

It is important that the location of the transducer 12 be as close as feasible to the bearing under test to maintain the measurement path as short as possible, although the present invention minimizes that importance compared to prior art practices. FIG. 3 depicts a raw acceleration signal generated from a typical flawed rolling element bearing, while FIG. 4 depicts the spectrum of that signal. FIG. 5 is the relative response of a typical bearing signal having a short measurement path between the bearing and the transducer 12 after being high pass filtered over a range of frequencies with numerical values noted at three commonly used filter cut-off frequencies in prior art systems which limit low frequency response to minimize interference. FIG. 6 is a similar plot for a long measurement path.

Figure 7:
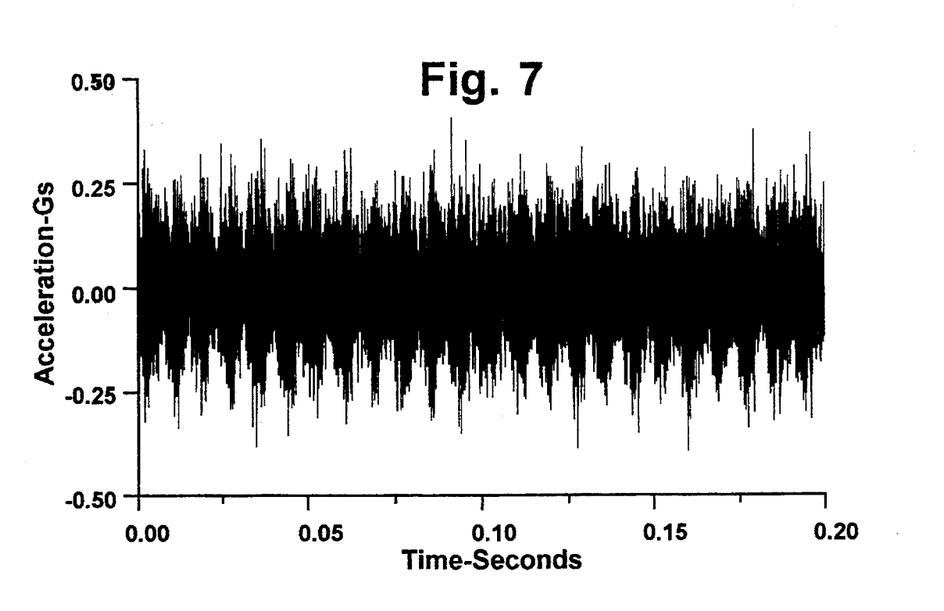
FIG. 7 is a graph depicting a time domain acceleration signal from a rolling element bearing source with interference present.
Figure 8:
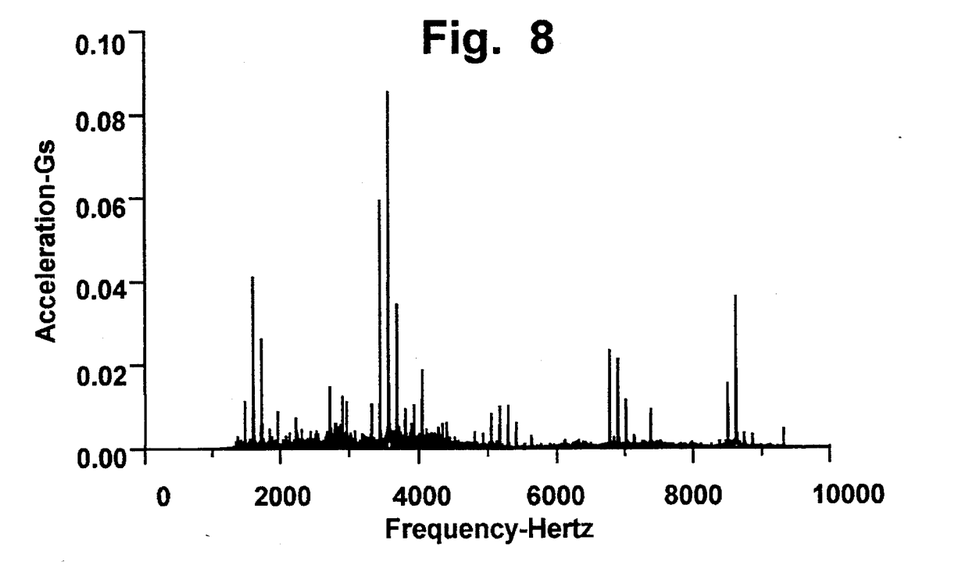
FIG. 8 is a graph depicting the spectrum of the signal of FIG. 7.
Figure 9:
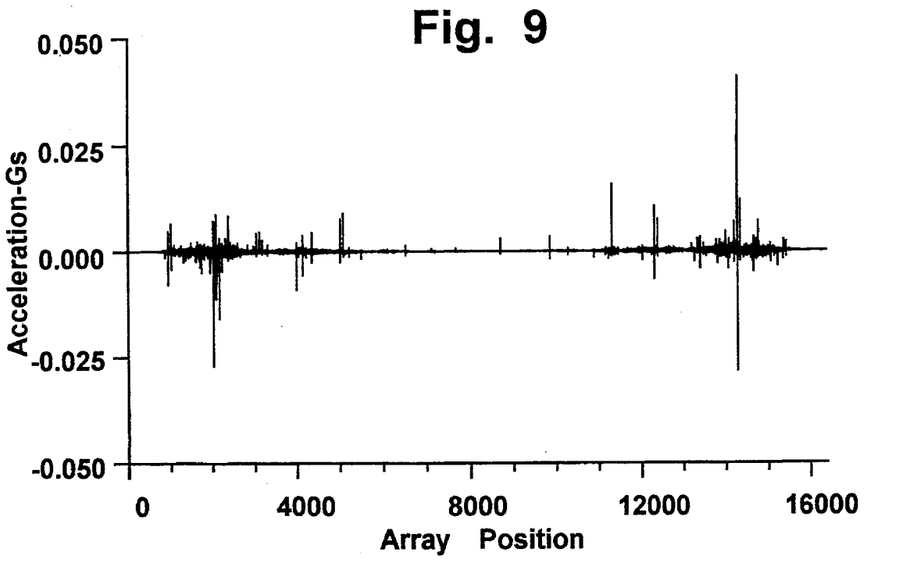
FIG. 9 is a graph depicting a time domain acceleration signal of FIG. 7 after being transformed to the frequency domain.
Figure 10:
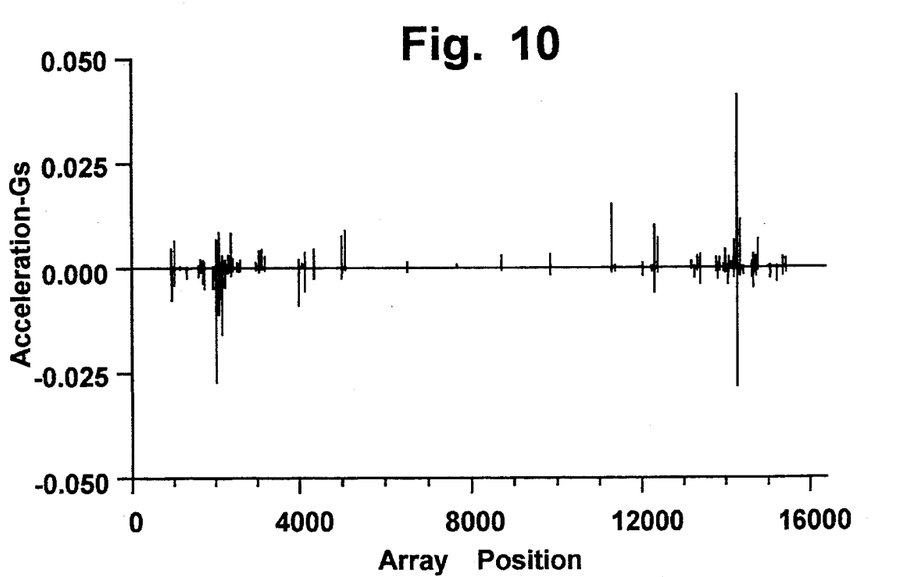
FIG. 10 is a graph depicting a frequency domain array containing interference signals.
Figure 11:
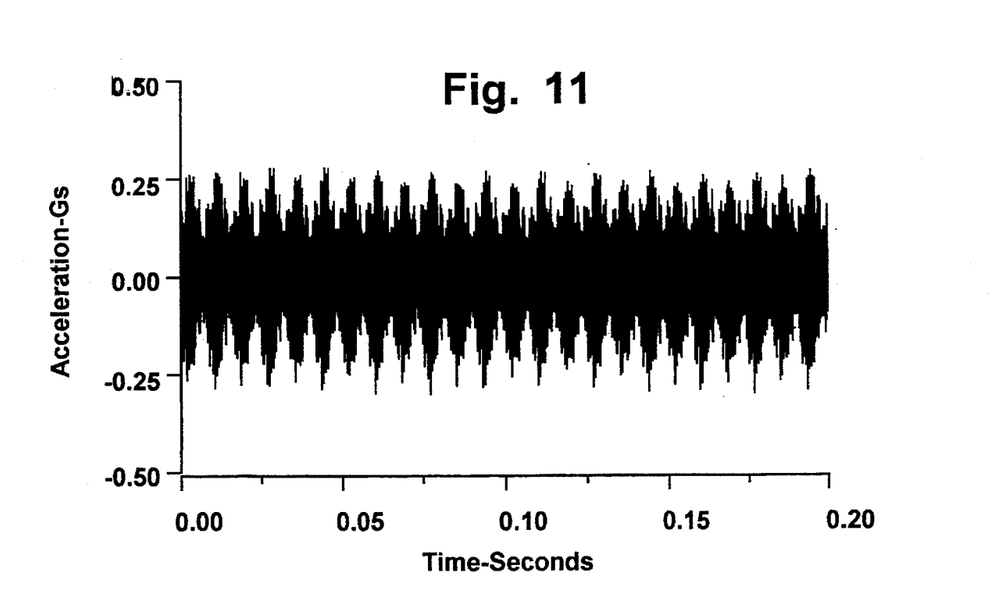
FIG. 11 is a graph depicting the data from FIG. 10 after being inverse transformed to the time domain.
Figure 12:
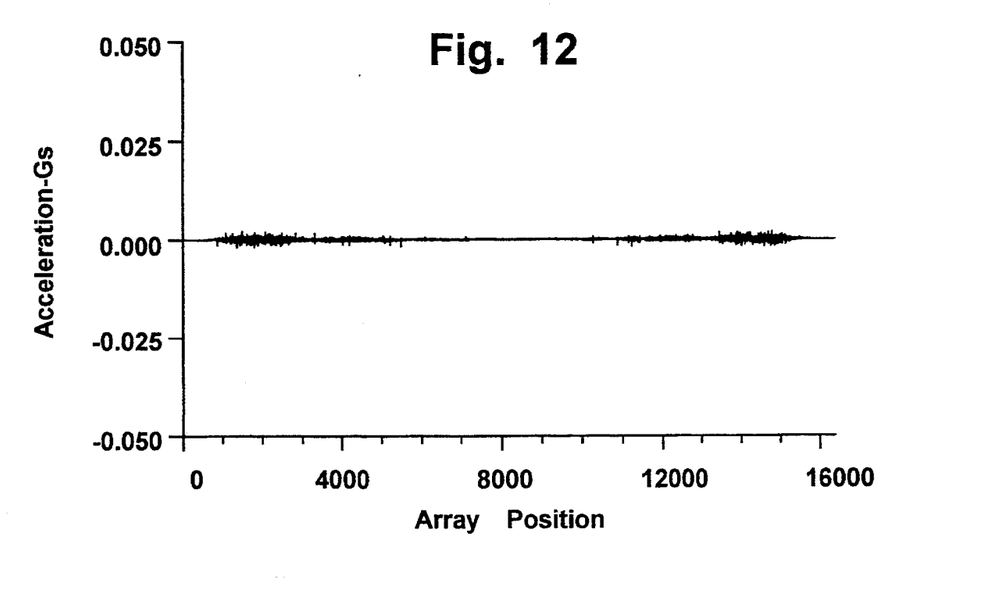
FIG. 12 is a graph depicting the frequency domain data of the normal filtered output signal and is the interference signal frequency domain data of FIG. 10 subtracted from the input signal frequency domain data of FIG. 9.
Figure 13:
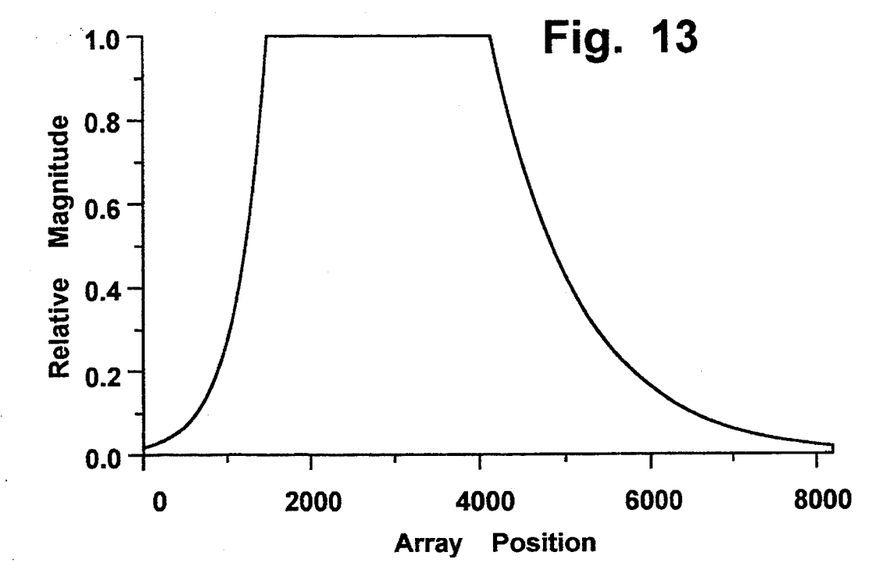
FIG. 13 is a graph depicting a compensation array simulating a typical rolling element bearing signal spectrum before the filter operations occur.
Figure 14:
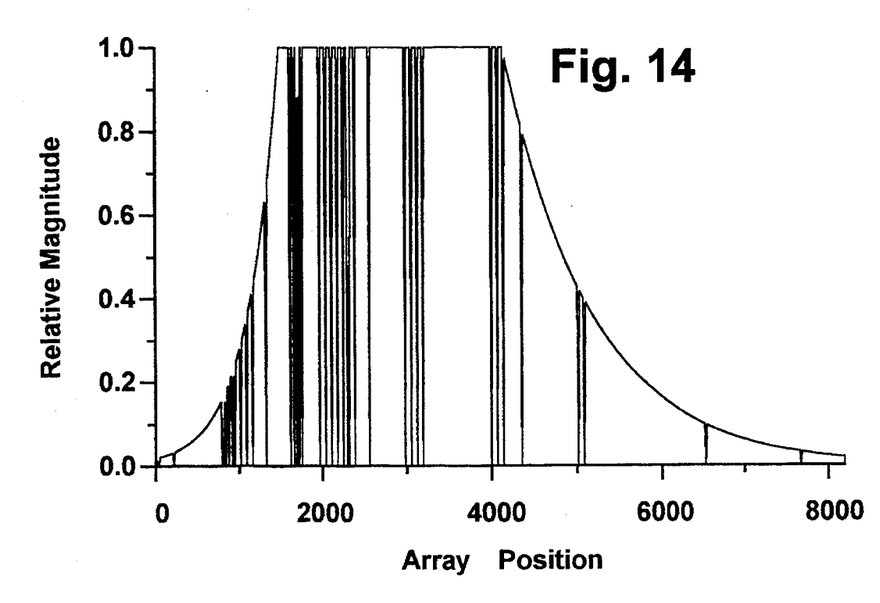
FIG. 14 is a graph depicting the data of FIG. 13 after the filter operations have occurred.
Figure 15:
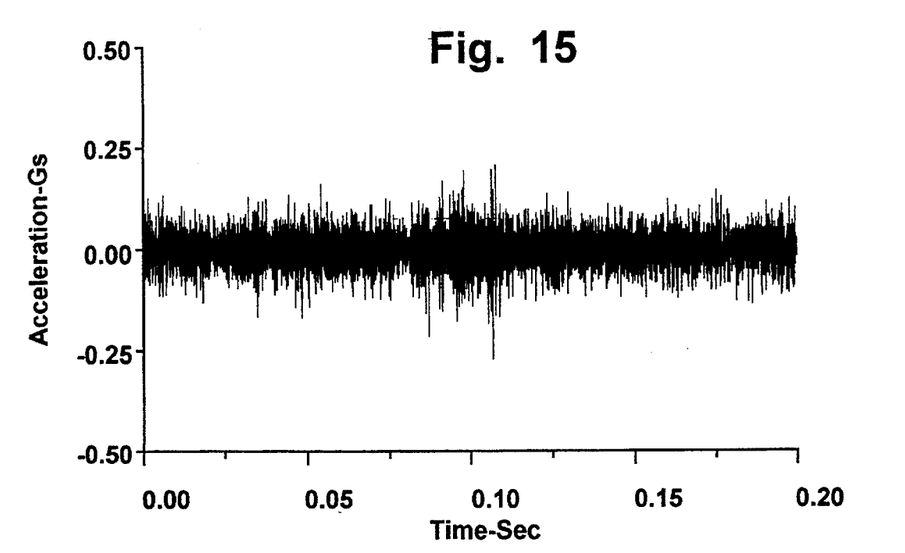
FIG. 15 is a graph depicting the normal output filtered data and is the data of FIG. 12 transformed to the time domain and scaled by the ratio of the sum of the squares of the data of FIG. 13 divided by the sum of the squares of the data of FIG. 14.
Figure 16:
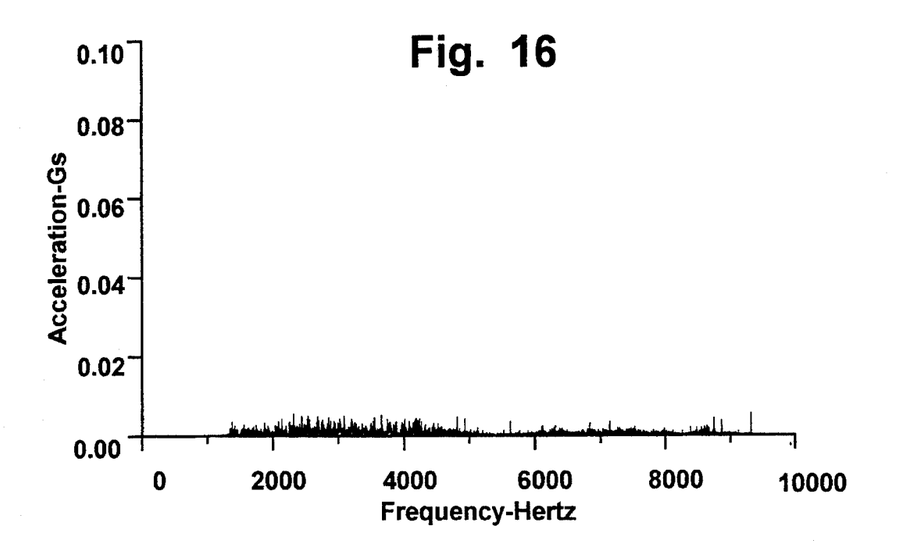
FIG. 16 is a graph depicting the spectrum of the signal of FIG. 15.

FIGS. 7 through 16 show waveforms of signals associated with the first embodiment of the testing apparatus 10. FIG. 7 is a time domain acceleration signal from a bearing source with interference present; for purposes of clarity, 0.2 second of the 0.64 second sample duration is displayed. FIG. 8 is the spectrum of the whole signal of FIG. 7. FIG. 9 is the time domain acceleration signal from FIG. 7 transformed to the frequency domain. This array contains 16,384 values in this example. Real(0) is off scale vertically and is not plotted. FIG. 10 is the frequency domain array containing the interference signals. This array may not normally exist as plotted as its data may be subtracted incrementally during the filtering operations if the interference signal output is not desired. Real(0) is off scale vertically and is not plotted. FIG. 11 is the data from FIG. 10 inverse transformed to the time domain. FIG. 12 is the frequency domain data of the normal filtered output signal and is the interference signal frequency domain data in FIG. 10 substracted from the input signal frequency domain data in FIG. 9. Real(0) is off scale vertically and is not plotted. FIG. 13 is the compensation array simulating a typical bearing signal spectrum before the filtering operations occur. Since the filtering operations were performed symmetrically for both the rear and imaginary halves of the frequency domain data, only half, 8192 points in this example, of the data array size is required. FIG. 14 is the date of FIG. 13 after the filtering operations have occurred. FIG. 15 is the normal output filtered data and is the data of FIG. 12 transformed to the time domain and scaled by the ratio of the sum of the squares of the data in FIG. 13 divided by the sum of the squares of the data in FIG. 14. The same 0.2 second time interval displayed in FIG. 7 is displayed in FIG. 15. FIG. 16 is the spectrum of the whole signal of FIG. 15.

Figure 17:
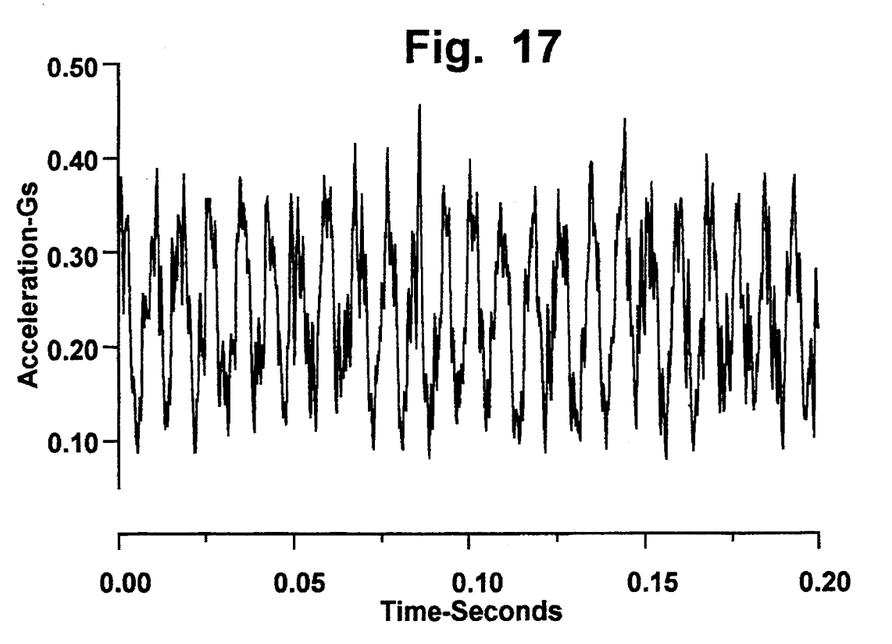
FIGS. 17 through 26 are graphs depicting envelope detected signal equivalents of the signals depicted in FIGS. 7 through 16.
Figure 18:
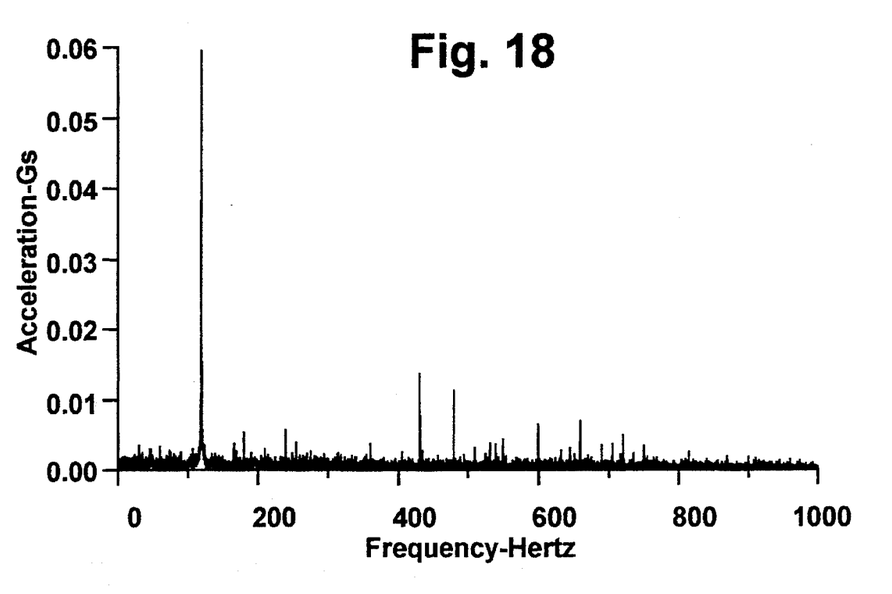
Figure 19:
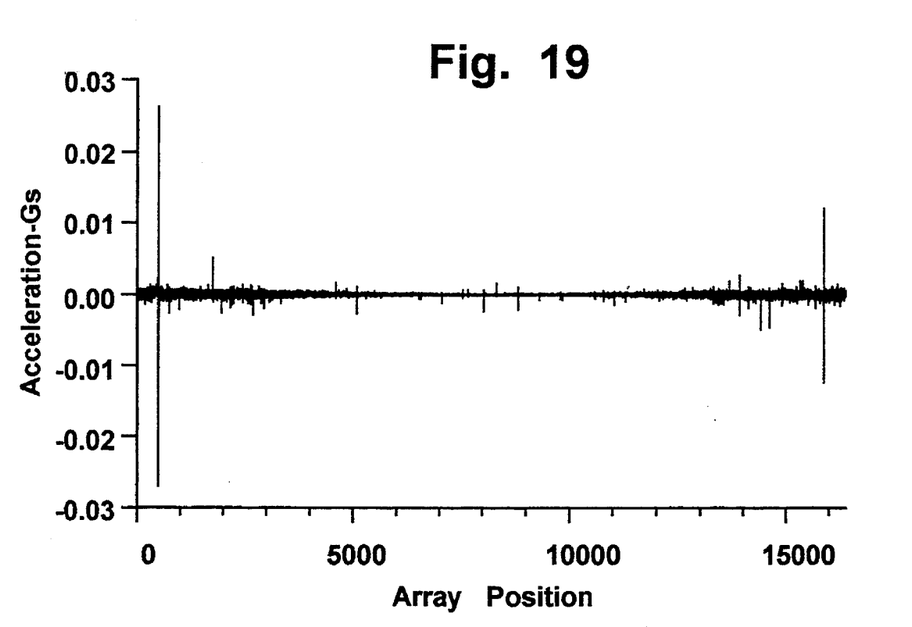
Figure 20:
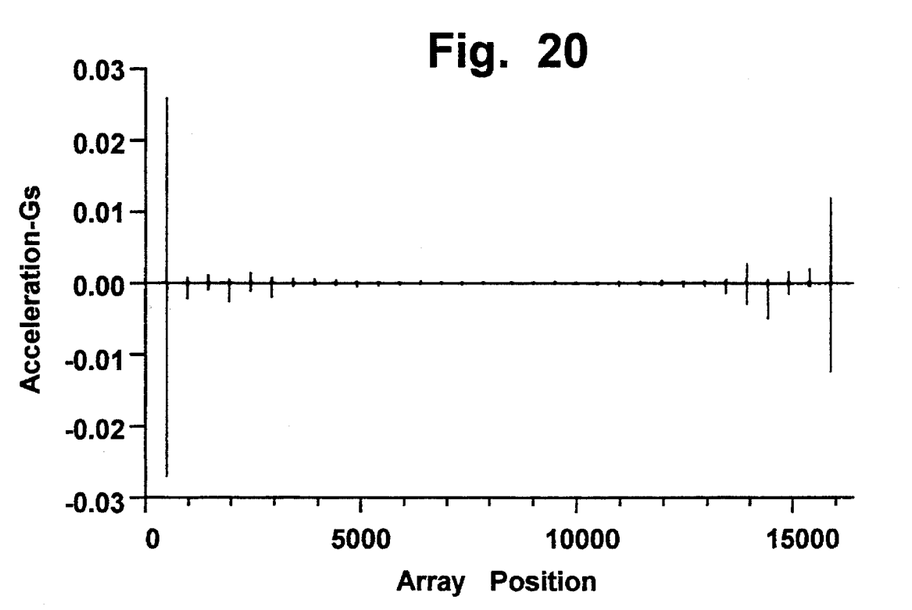
Figure 21:
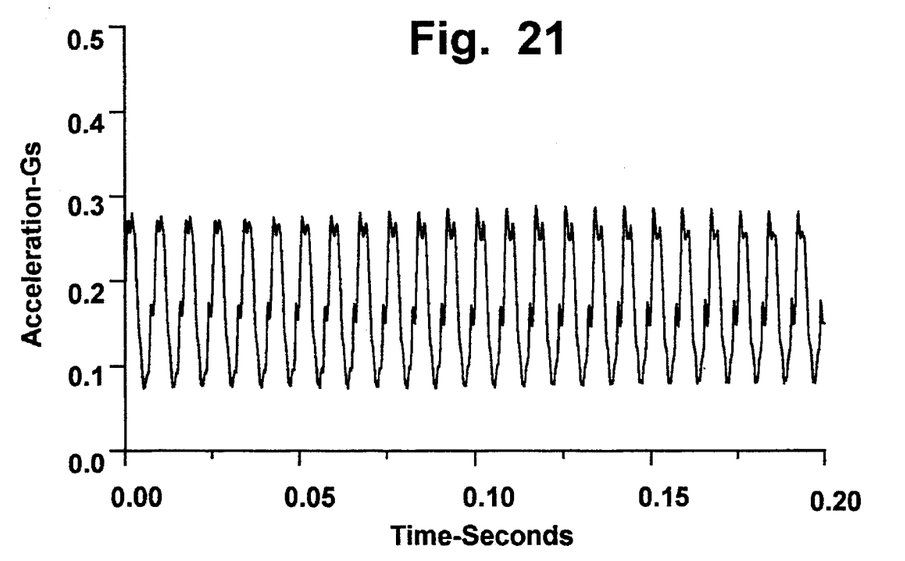
Figure 22:
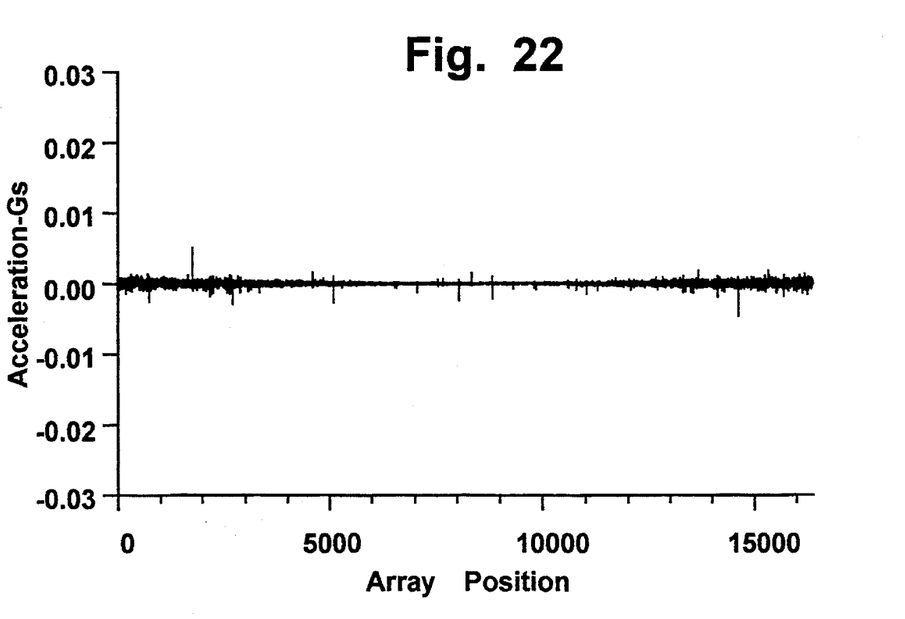
Figure 23:
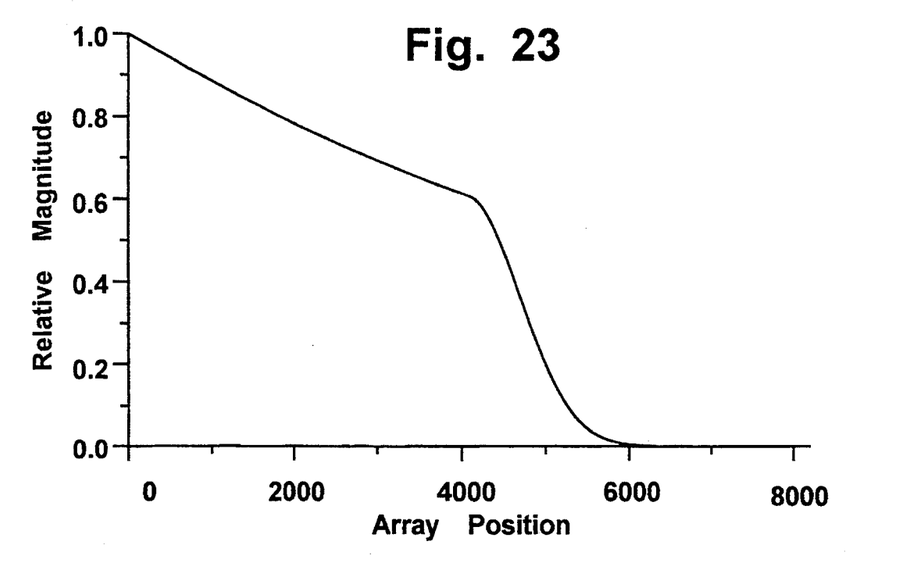
Figure 24:
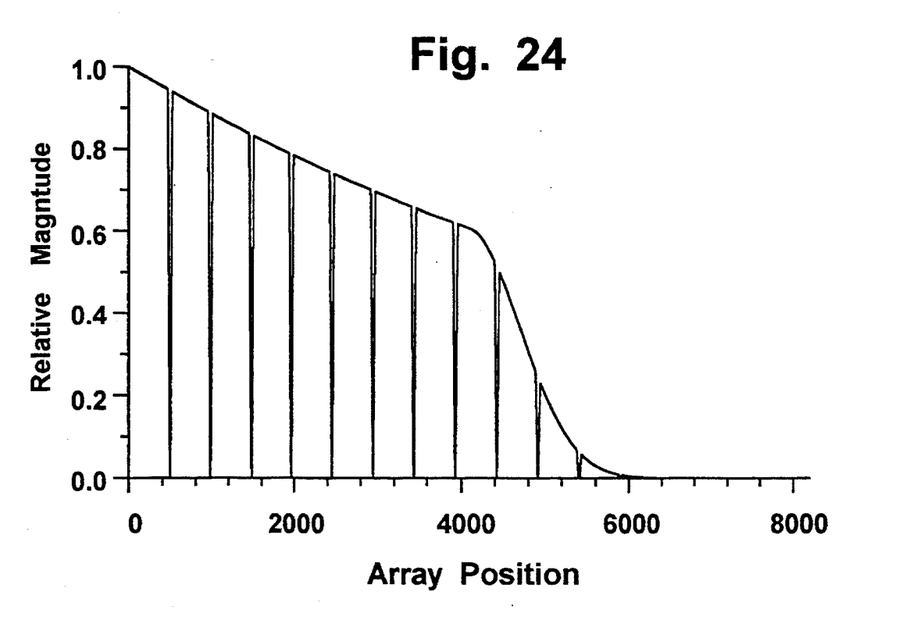
Figure 25:
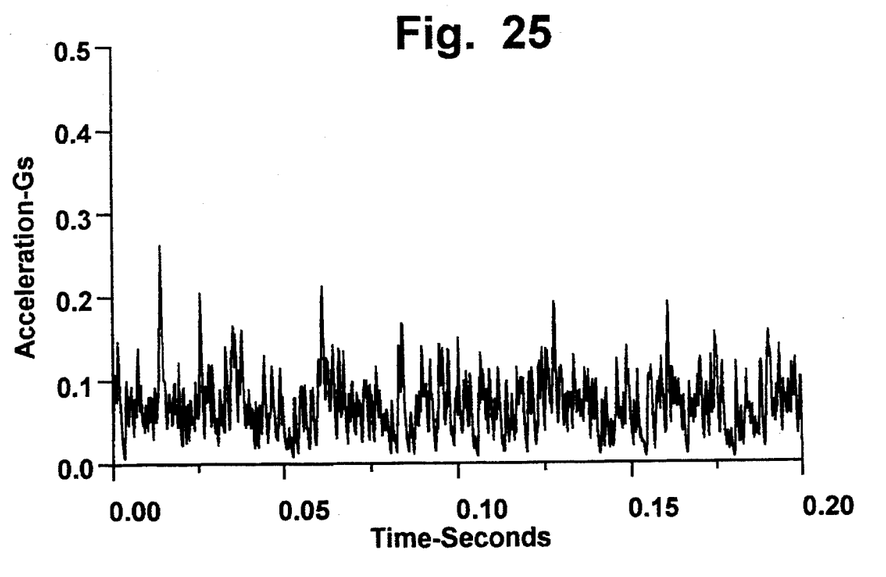
Figure 26:
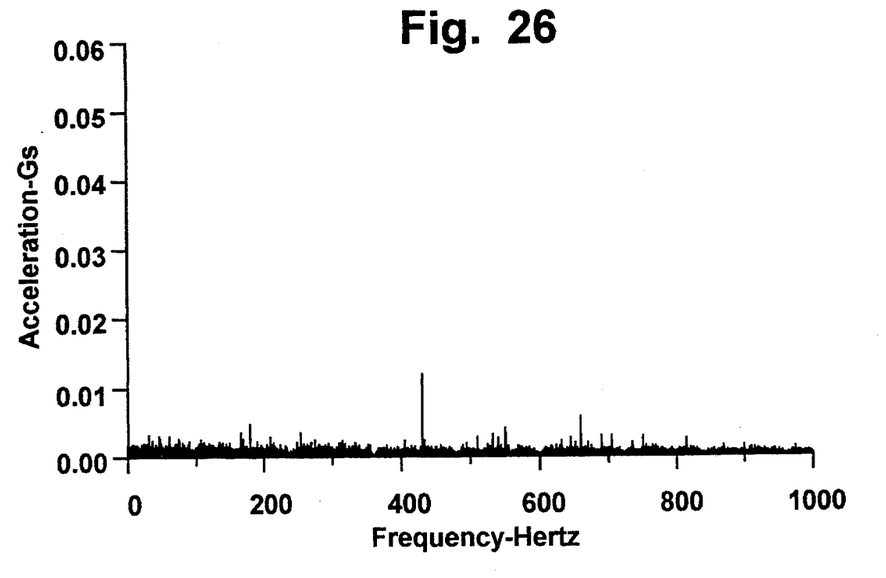

FIGS. 17 through 26 show waveforms of signals associated with the second embodiment of the testing apparatus 10. FIGS. 17 through 26 are the envelope detected signal equivalents of the signals displayed in FIGS. 7 through 16. FIG. 17 is a time domain envelope detected acceleration signal from a bearing source with interference present; for purposes of clarity, 0.2 second of the 6.4 second sample duration is displayed. FIG. 18 is the spectrum of the whole signal of FIG. 17. FIG. 19 is the time domain envelope detected acceleration signal from FIG. 17 transformed to the frequency domain. This array contains 16,384 values in this example. Real(0) is off scale vertically and is not plotted. FIG. 20 is the frequency domain array containing the interference signals. This array may not normally exist as plotted as its data may be subtracted incrementally during the filtering operations if the interference signal output is not desired. Real(0) is off scale vertically and is not plotted. FIG. 21 is the data from FIG. 20 inverse transformed to the time domain. FIG. 22 is the frequency domain data of the normal filtered output signal and is the interference signal frequency domain data in FIG. 20 substracted from the input signal frequency domain data in FIG. 19. Real(0) is off scale vertically and is not plotted. FIG. 23 is the compensation array simulating a typical bearing signal spectrum before the filtering operations occur. Since the filtering operations were performed symmetrically for both the rear and imaginary halves of the frequency domain data, only half, 8192 points in this example, of the data array size is required. FIG. 24 is the date of FIG. 23 after the filtering operations have occurred. FIG. 25 is the normal output filtered data and is the data of FIG. 22 transformed to the time domain and scaled by the ratio of the sum of the squares of the data in FIG. 23 divided by the sum of the squares of the data in FIG. 24. The same 0.2 second time interval displayed in FIG. 17 is displayed in FIG. 25. FIG. 26 is the spectrum of the whole signal of FIG. 25.

The rolling element bearing condition testing method of the present invention, by employing the first embodiment of the testing apparatus 10 of FIG. 1A, performs the steps of: detecting raw vibration signals emanating from the rolling bearing by employing the transducer 12, optionally band pass filtering the raw vibration signals by employing the band pass filtering first means 14 to provide output signals in the range of from 2,000 to 15,000 Hertz, converting the output signals from analog to digital format by employing the analog to digital converting second means 16 to provide digital output signals, and applying a selected one of a plurality of digital filtering techniques by employing the digital filtering third means 18 to remove the interference from the digital output signals and provide a digitally filtered signal. The digitally filtered signal is then applied to an output device 26, such as a display, storage or processor. Optionally, by employing the second embodiment of the testing apparatus 10 of FIG. 1B, the raw band passed filtered signals can be de-modulated (or envelope detected) by employing the envelope detecting or demodulating means 24 to provide a de-modulated (or envelope detected) output signals which are then analog to digital converted.

There are three digital filtering techniques which can be applied by the testing method and apparatus 10 of the present invention. These three digital filtering techniques, which will be described in detail hereinafter, are as follows: (1) separating interfering signals from the rolling element bearing output signals; (2) determining and selecting the frequencies of the interference to be removed; and (3) compensating the amplitude of rolling element bearing output signals for the portions of the rolling element bearing signals removed with the interference. The compensating step may be omitted in some instances. In the case of envelope detected signals, as opposed to raw signals, another filtering technique applied by the testing method of the present invention can also include reducing the average value of the rolling element bearing output signal corresponding to the reduction of the average level of the interference. These three digital filtering techniques are executed by a software program stored in the memory of and executed by a computer which program is exemplified by the flow chart of FIG. 2.

Interference Separation Technique

Figure 2:
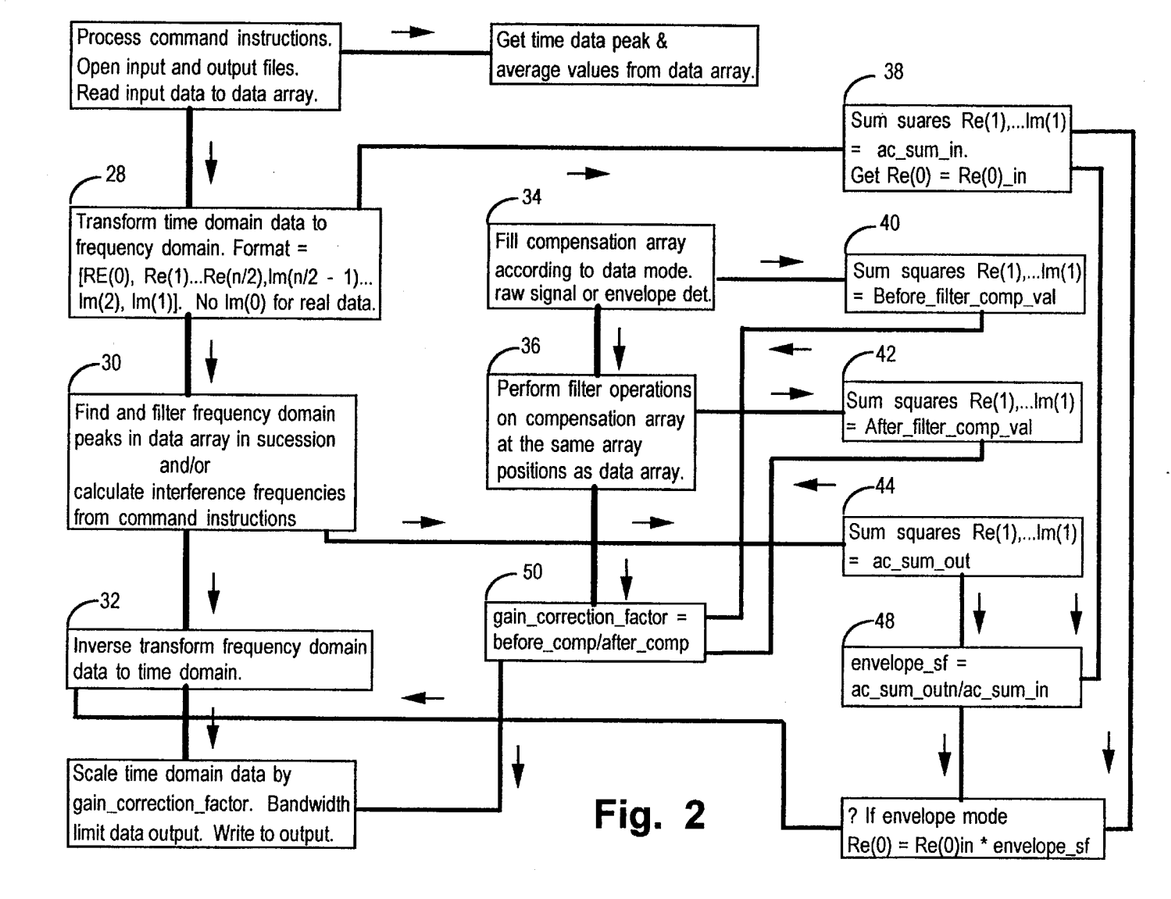
FIG. 2 is a flow chart outline a software program stored in the memory of and executed by a computer for applying first, second and third digital filtering techniques in the operation of the testing method and apparatus of the present invention.

As per blocks 28, 30 and 32 of the flow chart of FIG. 2, the basic filtering technique used to separate the bearing signals from interfering signals is a process referred to as Fourier Filtering, that is, using a Fast Fourier forward transform to convert the time domain signal to the frequency domain as a complex number array or arrays, filtering the signal in the frequency domain, and using an Fast Fourrier inverse transform to convert the signal back to the time domain. Other time to frequency domain transforms may also be used as well as other variations of the basic Fast Fourier Transform.

Fourier Filtering is especially useful when very narrow portions of a frequency spectrum are filtered. Using Fourier Filtering, the time domain signal is first transformed to the frequency domain, producing an array or pair of arrays, depending on the particular transform used, of numbers with a single value or pair of values corresponding to the average value of the signal array being processed and a pair or pairs of complex numbers, Real+Imaginery, corresponding to each frequency contained in the time domain signal. In the examples used herein, the frequency domain array has the format= [Real(0), Real(1), . . . , Real(n/2), Imaginary(n/2–1), . . . , Imaginery(1)] where n is the number of data points in the array, Real(0) is the average or d.c. value of the signal, and the remaining array values correspond to the a.c. or time varying values of the signal. In this process, the interference selected may be selected in the frequency domain, inverse transformed to the time domain, and subtracted from the original signal in the time domain or the interference may be removed in the frequency domain followed by inverse transformation of remaining frequency domain signal back to the time domain.

The two approaches yield similar results, although removal of the interference in the frequency domain and transformation back to the time domain is substantially more efficient computationally in terms of the needed calculations and the memory requirements. Blocks of array points corresponding to the real and imaginary frequencies of the interference are selected and either added to the array values of a second frequency domain array if the interference is to be selected for transformation back to the time domain or subtracted from the original frequency domain array if the interference is to be removed in the frequency domain before transformation back to the time domain.

Multiplying the interference signals by a tapered window function such as a Hanning Window is desirable and was done in the examples herein. The blocks of frequencies surrounding each interference frequency may be multiplied by one (1) minus the window function if the interference signal is not to be sent to output.

Interference Frequency Selection Technique

As per block 30 of the flow chart of FIG. 2, the selection of the interfering frequencies to be removed may either be done automatically within the program if the frequencies of the interference are not known precisely, which is the case for the raw signal (not demodulated) induction motor used as an example here, be specified to the program if the interference frequency characteristics are known precisely, as in the case for the envelope detected induction motor example used herein. Also, interfering frequencies to be removed may be specified as a signal level or as a percentage of maximum spectral value of the interference or may be estimated as a function of the crest factor and sample length of the time domain being filtered.

Electrical excitation of an induction motor produces groups of signals at frequencies determined by the construction and rotating frequency or speed of the motor which are modulated at even integral multiples of the motor power source frequency. Since speed is a variable and construction details are frequently not known, the program must select the frequencies of the interference if the raw signal is to be processed.

If the demodulated (envelope detected) signal is to be processed, the interfering signals (2, 4, 6, 8, ... times power line frequency) are usually known precisely and can be specified to the filter program. Automatic selection of the interfering frequencies by the filter program can be accomplished in the following manner.

The signals which the bearings generate are essentially modified impulse signals having a high peak to average ratio or crest factor in the time domain and are best characterized as successions of individual events. Conversely, almost all signals that are interfering signals are essentially low crest factor or continuous signals. If a time domain signal sample containing a mixture of bearing signals and interfering signals is transformed to the frequency domain, the bearing signals will correspond to a continuous, nonuniform, relatively low level, distribution or spread of frequencies throughout the frequency spectrum and the interference will be found in a relatively higher amplitude frequency, harmonic series of frequencies, or groups of frequencies. In the frequency domain, the interfering signal will have a high peak to average ratio compared to the bearing signals, the opposite case from the time domain. The program can separate the interference by successively locating and removing frequency domain peaks, either until a predetermined frequency domain peak to average ratio is reached or by stopping the process when the time domain crest factor is maximized, which corresponds to minimizing the frequency domain peak to average ratio of the signal, a simple comparison test of which can be taken at each step of the frequency domain peak location and subtraction process.

Signal Reduction Compensation Technique

As per blocks 34 and 36 of the flow chart of FIG. 2, since the bearing signals have a relatively broad, continuous distribution or spread of frequencies, portions of their spectra can be removed without significantly changing their overall character except by reducing their amount. The reduction in bearing signal levels produced by removing portions of their spectrum can be compensated for by creating an array comparable to the frequency domain distribution of the bearing signal and, after performing the same filtering operations on the compensation array as were performed of the bearing signal array, scaling the bearing filter output signal by the ratio of the sum of the squares of the compensation array values before filtering to the sum of the squares of the compensation array values after its filter operations are performed, with the zero frequency value(s) of the compensation array equal zero or not included. If the filter operations are performed symmetrically in both the Real and Imaginary sides of the signal frequency domain array, as was the case in the included examples, then one side of the compensation array may be omitted. In addition, the average value of an envelope detected signal should be increased by the ratio of the sum of the squares of the time varying (non-average) component of bearing signal in the frequency domain before filtering to sum of the squares of the time varying (non-average) component of bearing signal in the frequency domain after filtering. This may be accomplished by scaling the average or d.c. value of the frequency domain, Real(0), before that array is transformed back to the time domain to generate the output signal.

In the flow chart of FIG. 2, the blocks 38–50 represent the various mathematical computations that occur to generate scale factors in the above-described three filtering techniques.

Recapitulation

In summary, the rolling element bearing condition testing method and apparatus of the present invention overcomes the disadvantages associated with the prior art practices of higher frequency band limited rolling element bearing vibration measurements or measurements which use spectra analysis of the raw signal or use the envelope detected signal to distinguish between the rolling element bearing emitted signals and the interference signals. The rolling element bearing condition testing method and apparatus of the present invention measures the time domain vibration signals generated by the rolling element bearing in the frequency range containing the majority of the rolling bearing energy, typically from about 2,000 to 15,000 Hertz, optionally de-modulates those signals, and then uses digital filter techniques to remove the interference, either from the demodulated acceleration signal or from the raw acceleration signal. The different filtering techniques applied by the testing method are as follows: (a) separating interfering signals from the rolling element bearing output signals; (b) determining the frequencies of the interfering frequencies to be removed; and (c) compensating the amplitude of rolling element bearing output signals for the portions of the rolling element bearing signals removed with the interference. The compensating step may be omitted in some cases. In the case of envelope detected signals, as opposed to raw signals, the testing method may also include the step of reducing the average value of the rolling bearing output signal corresponding to the reduction of the average level of the interference.

It is thought that the present invention and its advantages will be understood from the foregoing description and it will be apparent that various changes may be made thereto without departing from the spirit and scope of the invention or sacrificing all of its material advantages, the form hereinbefore described being merely an exemplary embodiment thereof.

I claim:

1. A method for testing rolling element bearing condition, comprising the steps of:
    (a) detecting raw vibration signals emitted from a rolling bearing;
    (b) de-modulating the raw vibration signals to provide de-modulated output signals;
    (c) converting the raw vibration de-modulated output signals from analog to digital format to provide digital output signals;
    (d) applying a selected one of a plurality of digital filtering techniques to the digital output signals to remove interference from the digital output signals and provide a digitally filtered signal; and
    (e) outputting the digitally filtered signal to an output device.

2. A method for testing rolling element bearing condition, comprising the steps of:
    (a) detecting raw vibration signals emitted from a rolling bearing;
    (b) band pass filtering the raw vibration signals to provide output signals in the range of from 2,000 to 15,000 Hertz;
    (c) converting the output signals from analog to digital format to provide digital output signals;
    (d) applying a selected one of a plurality of digital filtering techniques to the digital output signals to remove interference from the digital output signals and provide a digitally filtered signal; and (e) outputting the digitally filtered signal to an output device.

3. The method of claim 2 wherein said band pass filtering includes high pass filtering the raw vibration signals.

4. The method of claim 2 wherein said band pass filtering includes low pass filtering the raw vibration signals.

5. The method of claim 4 wherein said band pass filtering includes high pass filtering the raw vibration signals.

6. The method of claim 5 further comprising:

de-modulating the raw band pass filtered signals to provide de-modulated output signals which are then converted from analog to digital format.

7. A method for testing rolling element bearing condition, comprising the steps of:

(a) detecting raw vibration signals emitted from a rolling bearing;

(b) converting the raw vibration signals from analog to digital format to provide digital output signals;

(c) applying a selected one of a plurality of digital filtering techniques to the digital output signals to remove interference from the digital output signals and provide a digitally filtered signal, said digital filtering techniques including the step of separating interfering signals from the digital output signals; and (e) outputting the digitally filtered signal to an output device.

8. The method of claim 7 wherein said digital filtering techniques include the step of determining and selecting the frequencies of the interference to be removed.

9. The method of claim 7 wherein said digital filtering techniques include the step of compensating the amplitude of rolling element raw vibration signals for the portions of the digital output signals removed with the interference.

10. An apparatus for testing rolling element bearing condition, comprising:

(a) means for detecting raw vibration signals emitted from a rolling element bearing;

(b) means for de-modulating the raw vibration signals to provide de-modulated output signals;

(c) means for converting the de-modulated output signals from analog to digital format to provide digital output signals; and (d) means for applying a selected one of a plurality of digital filtering techniques to the digital output signals to remove interference from the digital output signals and provide a digitally filtered signal and for outputting the digitally filtered signal to an output device.

11. An apparatus for testing rolling element bearing condition, comprising:

(a) means for detecting raw vibration signals emitted from a rolling element bearing;

(b) means for band pass filtering the raw vibration signals to provide output signals in the range of from 2,000 to 15,000 Hertz;

(c) means for converting the output signals from analog to digital format to provide digital output signals; and (d) means for applying a selected one of a plurality of digital filtering techniques to the digital output signals to remove interference from the digital output signals and provide a digitally filtered signal and for outputting the digitally filtered signal to an output device.

12. The apparatus of claim 11 wherein said band pass filtering means includes means for high pass filtering the raw vibration signals.

13. The apparatus of claim 11 wherein said band pass filtering means includes means for low pass filtering the raw vibration signals.

14. The apparatus of claim 13 wherein said band pass filtering means includes means for high pass filtering the raw vibration signals.

15. The apparatus of claim 14 further comprising:

means for de-modulating the raw high and low pass filtered signals to provide de-modulated output signals which are then converted from analog to digital format.

16. An apparatus for testing rolling element bearing condition, comprising:

(a) means for detecting raw vibration signals emitted from a rolling element bearing;

(b) means for converting the raw vibration signals from analog to digital format to provide digital output signals; and (c) means for applying a selected one of a plurality of digital filtering techniques to the digital output signals to remove interference from the digital output signals and provide a digitally filtered signal and for outputting the digitally filtered signal to an output device, said digital filtering techniques applying means including means for separating interfering signals from the digital output signals.

17. The apparatus of claim 16 wherein said digital filtering techniques applying means includes means for determining and selecting the frequencies of the interference to be removed.

18. The apparatus of claim 16 wherein said digital filtering techniques applying means includes means for compensating the amplitude of rolling element raw vibration signals for the portions of the digital output signals removed with the interference.

* * * * *